(12) United States Patent
Al-Ali

(10) Patent No.: US 7,509,494 B2
(45) Date of Patent: Mar. 24, 2009

(54) INTERFACE CABLE

(75) Inventor: Ammar Al-Ali, Tustin, CA (US)

(73) Assignee: Masimo Corporation, Irvine, CA (US)

( * ) Notice: Subject to any disclaimer, the term of this patent is extended or adjusted under 35 U.S.C. 154(b) by 952 days.

(21) Appl. No.: 10/377,996

(22) Filed: Feb. 28, 2003

(65) Prior Publication Data

US 2003/0167391 A1 Sep. 4, 2003

Related U.S. Application Data

(60) Provisional application No. 60/381,393, filed on May 16, 2002, provisional application No. 60/361,233, filed on Mar. 1, 2002.

(51) Int. Cl.
*H04L 9/00* (2006.01)
*A61B 5/00* (2006.01)

(52) U.S. Cl. .................. 713/168; 713/169; 713/170; 713/171; 726/2; 726/26; 600/310; 600/323

(58) Field of Classification Search ......... 713/168–169, 713/182; 600/310, 323, 331; 726/2, 26
See application file for complete search history.

(56) References Cited

U.S. PATENT DOCUMENTS

| | | | |
|---|---|---|---|
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |
| 5,163,438 A | 11/1992 | Gordon et al. | |
| 5,287,853 A * | 2/1994 | Vester et al. ............. | 600/323 |
| 5,337,744 A | 8/1994 | Branigan | |
| D353,195 S | 12/1994 | Savage et al. | |
| D353,196 S | 12/1994 | Savage et al. | |
| 5,431,170 A | 7/1995 | Mathews | |
| D361,840 S | 8/1995 | Savage et al. | |
| D362,063 S | 9/1995 | Savage et al. | |
| 5,452,717 A | 9/1995 | Branigan et al. | |
| D363,120 S | 10/1995 | Savage et al. | |
| 5,482,036 A | 1/1996 | Diab et al. | |

(Continued)

FOREIGN PATENT DOCUMENTS

EP 1 169 965 A1 1/2002

(Continued)

OTHER PUBLICATIONS

PCT International Search Report, App. No. PCT/US03/06548, App. Date: Mar. 3, 2003, 4 pages.

*Primary Examiner*—Kambiz Zand
*Assistant Examiner*—Yin-Chen Shaw
(74) *Attorney, Agent, or Firm*—Knobbe, Martens, Olson & Bear LLP

(57) ABSTRACT

An interface cable is configured to connect a host instrument to a physiological sensor. The interface cable has an ID signal input from the sensor and a LED drive signal input from the host instrument sensor port. The interface cable also has a data signal output to the host instrument sensor port. The LED drive signal and the data signal provide an encrypted handshake to and from the host instrument. The handshake is responsive to the ID signal so as to enable normal operation of the host instrument and the sensor.

24 Claims, 14 Drawing Sheets

U.S. PATENT DOCUMENTS

| | | | |
|---|---|---|---|
| 5,490,505 A | 2/1996 | Diab et al. | |
| 5,494,043 A | 2/1996 | O'Sullivan et al. | |
| 5,533,511 A | 7/1996 | Kaspari et al. | |
| 5,562,002 A | 10/1996 | Lalin | |
| 5,590,649 A | 1/1997 | Caro et al. | |
| 5,602,924 A | 2/1997 | Durand et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,807,247 A * | 9/1998 | Merchant et al. | 600/310 |
| 5,810,734 A | 9/1998 | Caro et al. | |
| 5,818,985 A * | 10/1998 | Merchant et al. | 385/20 |
| 5,823,950 A | 10/1998 | Diab et al. | |
| 5,830,131 A | 11/1998 | Caro et al. | |
| 5,833,618 A | 11/1998 | Caro et al. | |
| 5,860,919 A | 1/1999 | Kiani-Azarbayjany et al. | |
| 5,890,929 A | 4/1999 | Mills et al. | |
| 5,904,654 A | 5/1999 | Wohltmann et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,995,855 A | 11/1999 | Kiani et al. | |
| 5,995,858 A * | 11/1999 | Kinast | 600/323 |
| 5,997,343 A | 12/1999 | Mills et al. | |
| 6,002,952 A | 12/1999 | Diab et al. | |
| 6,011,986 A * | 1/2000 | Diab et al. | 600/323 |
| 6,027,452 A | 2/2000 | Flaherty et al. | |
| RE36,620 E * | 3/2000 | Costello, Jr. | 250/252.1 |
| 6,036,642 A | 3/2000 | Diab et al. | |
| 6,045,509 A | 4/2000 | Caro et al. | |
| 6,067,462 A | 5/2000 | Diab et al. | |
| 6,081,735 A | 6/2000 | Diab et al. | |
| 6,088,607 A | 7/2000 | Diab et al. | |
| 6,110,522 A | 8/2000 | Lepper, Jr. et al. | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,236,872 B1 | 5/2001 | Diab et al. | |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,298,255 B1 * | 10/2001 | Cordero et al. | 600/372 |
| 6,308,089 B1 * | 10/2001 | von der Ruhr et al. | 600/338 |
| 6,321,100 B1 | 11/2001 | Parker | |
| 6,334,065 B1 | 12/2001 | Al-Ali et al. | |
| 6,343,224 B1 | 1/2002 | Parker | |
| 6,349,228 B1 | 2/2002 | Kiani et al. | |
| 6,360,114 B1 | 3/2002 | Diab et al. | |
| 6,367,017 B1 * | 4/2002 | Gray | 726/9 |
| 6,371,921 B1 | 4/2002 | Caro et al. | |
| 6,377,829 B1 | 4/2002 | Al-Ali | |
| 6,388,240 B2 | 5/2002 | Schulz et al. | |
| 6,397,091 B2 | 5/2002 | Diab et al. | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,497,659 B1 * | 12/2002 | Rafert | 600/331 |
| 6,501,975 B2 | 12/2002 | Diab et al. | |
| 6,515,273 B2 | 2/2003 | Al-Ali | |
| 6,519,487 B1 | 2/2003 | Parker | |
| 6,525,386 B1 | 2/2003 | Mills et al. | |
| 6,526,300 B1 | 2/2003 | Kiani et al. | |
| 6,541,756 B2 | 4/2003 | Schulz et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,585,660 B2 * | 7/2003 | Dorando et al. | 600/486 |
| 6,595,316 B2 | 7/2003 | Cybulski et al. | |
| 6,597,933 B2 | 7/2003 | Kiani et al. | |
| 6,606,511 B1 | 8/2003 | Ali et al. | |
| 6,628,975 B1 * | 9/2003 | Fein et al. | 600/323 |
| 6,632,181 B2 | 10/2003 | Flaherty et al. | |
| 6,640,116 B2 | 10/2003 | Diab | |
| 6,643,530 B2 | 11/2003 | Diab et al. | |
| 6,650,917 B2 | 11/2003 | Diab et al. | |
| 6,654,624 B2 | 11/2003 | Diab et al. | |
| 6,658,276 B2 | 12/2003 | Diab et al. | |
| 6,661,161 B1 | 12/2003 | Lanzo et al. | |
| 6,665,551 B1 * | 12/2003 | Suzuki | 600/322 |
| 6,671,531 B2 | 12/2003 | Al-Ali et al. | |
| 6,678,543 B2 | 1/2004 | Diab et al. | |
| 6,684,090 B2 | 1/2004 | Ali et al. | |
| 6,684,091 B2 | 1/2004 | Parker | |
| 6,697,656 B1 | 2/2004 | Al-Ali | |
| 6,697,658 B2 | 2/2004 | Al-Ali | |
| RE38,476 E | 3/2004 | Diab et al. | |
| 6,699,194 B1 | 3/2004 | Diab et al. | |
| 6,714,804 B2 | 3/2004 | Al-Ali et al. | |
| RE38,492 E | 4/2004 | Diab et al. | |
| 6,721,585 B1 | 4/2004 | Parker | |
| 6,725,075 B2 | 4/2004 | Al-Ali | |
| 6,735,459 B2 | 5/2004 | Parker | |
| 6,745,060 B2 | 6/2004 | Diab et al. | |
| 6,760,607 B2 | 7/2004 | Al-All | |
| 6,770,028 B1 | 8/2004 | Ali et al. | |
| 6,771,994 B2 | 8/2004 | Kiani et al. | |
| 6,792,300 B1 | 9/2004 | Diab et al. | |
| 6,813,511 B2 | 11/2004 | Diab et al. | |
| 6,816,741 B2 | 11/2004 | Diab | |
| 6,822,664 B2 | 11/2004 | Al-Ali | |
| 6,826,419 B2 | 11/2004 | Diab et al. | |
| 6,830,711 B2 | 12/2004 | Mills et al. | |
| 6,850,787 B2 | 2/2005 | Weber et al. | |
| 6,850,788 B2 | 2/2005 | Al-Ali | |
| 6,852,083 B2 | 2/2005 | Caro et al. | |
| 6,861,639 B2 | 3/2005 | Al-Ali | |
| 6,898,452 B2 | 5/2005 | Al-Ali et al. | |
| 6,920,345 B2 | 7/2005 | Al-Ali et al. | |
| 6,931,268 B1 | 8/2005 | Kiani-Azarbayjany et al. | |
| 6,934,570 B2 | 8/2005 | Kiani et al. | |
| 6,939,305 B2 | 9/2005 | Flaherty et al. | |
| 6,943,348 B1 | 9/2005 | Coffin IV | |
| 6,950,687 B2 | 9/2005 | Al-Ali | |
| 6,961,598 B2 | 11/2005 | Diab | |
| 6,970,792 B1 | 11/2005 | Diab | |
| 6,979,812 B2 | 12/2005 | Al-Ali | |
| 6,985,764 B2 | 1/2006 | Mason et al. | |
| 6,993,371 B2 | 1/2006 | Kiani et al. | |
| 6,996,427 B2 | 2/2006 | Ali et al. | |
| 6,999,904 B2 | 2/2006 | Weber et al. | |
| 7,003,338 B2 | 2/2006 | Weber et al. | |
| 7,003,339 B2 | 2/2006 | Diab et al. | |
| 7,015,451 B2 | 3/2006 | Dalke et al. | |
| 7,024,233 B2 | 4/2006 | Ali et al. | |
| 7,027,849 B2 | 4/2006 | Al-Ali | |
| 7,030,749 B2 | 4/2006 | Al-Ali | |
| 7,039,449 B2 | 5/2006 | Al-Ali | |

| | | |
|---|---|---|
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |

| | | | |
|---|---|---|---|
| 2003/0073890 A1* | 4/2003 | Hanna | 600/323 |
| 2003/0145646 A1* | 8/2003 | Henry et al. | 73/19.1 |

FOREIGN PATENT DOCUMENTS

WO     WO 00/61003     10/2000

* cited by examiner

INTERFACE CABLE

REFERENCE TO RELATED APPLICATION

The present application claims priority benefit under 35 U.S.C. §119(e) from U.S. Provisional Application No. 60/381,393, filed May 16, 2002, entitled "*Encryption Interface Cable,*" and from U.S. Provisional Application No. 60/361,233 filed Mar. 1, 2002, entitled "*Encryption Interface Cable,*" which are incorporated herein by reference.

BACKGROUND OF THE INVENTION

Pulse oximetry is a widely accepted noninvasive procedure for measuring the oxygen saturation level of arterial blood. FIG. 1 illustrates a pulse oximetry system 100 having a sensor 200 attachable to a patient 10, a host instrument 310 for monitoring oxygen saturation and pulse rate, and a patient cable 350 that connects the sensor 200 and the host instrument 310. The sensor 200, can be attached to an adult patient's finger or an infant patient's foot, for example.

FIG. 2 illustrates a sensor 200 having both red and infrared LEDs 210 and a photodiode detector 220. The sensor 200 is configured so that the LEDs 210 project light through the blood vessels and capillaries of a tissue site. The photodiode 220 is positioned at the tissue site opposite the LEDs 210 so as to detect the LED emitted light as it emerges from the tissue site. The sensor 200 has LED pinouts 240 and photodiode pinouts 250 that provide a connection to the host instrument 310 (FIG. 1) via the patient cable 350 (FIG. 1). A pulse oximetry sensor is described in U.S. Pat. No. 6,256,523 entitled "Low-Noise Optical Probes," assigned to Masimo Corporation, Irvine, Calif. and incorporated by reference herein.

As shown in FIG. 2, the sensor 200 may also have a identification (ID) element 230. The ID element 230 may be any circuit element, such as a resistor having a predetermined value, that provides information regarding the sensor 200. This information may be used, for example, to indicate the sensor manufacturer or supplier. The ID element 230 may be located in parallel with the LEDs 210 so as to share the LED pinouts 240. The host instrument 310 (FIG. 1) may be programmed to operate only if it is connected to a sensor 200 that it recognizes is from an authorized source. This feature maintains sensor and measurement quality control and ensures patient safety. Sensor identification and information elements and are described in U.S. Pat. No. 6,011,986 entitled "Manual And Automatic Probe Calibration," which is assigned to Masimo Corporation, Irvine, Calif. and incorporated by reference herein.

FIG. 3 functionally illustrates a pulse oximetry system 100 having a sensor 200, a host instrument 310 and a patient cable 350. The host instrument 310 has LED drivers 312 that alternately activate the sensor red and IR LEDs 210. A signal conditioner 315 processes the resulting current generated by the photodiode detector 220, which is proportional to the intensity of the detected light. A signal processor 316 inputs the conditioned detector signal and determines oxygen saturation based on the differential absorption by arterial blood of the two wavelengths emitted by the LEDs 210. Specifically, a ratio of detected red and infrared intensities is calculated by the signal processor 316, and an arterial oxygen saturation value is empirically determined based on the ratio obtained. Computed oxygen saturation and pulse rate are provided on the host instrument display 318. An ID reader 314 is capable of determining the ID element 230. A host instrument signal processor is described in U.S. Pat. No. 6,081,735 entitled "Signal Processing Apparatus," which is assigned to Masimo Corporation, Irvine, Calif. and incorporated by reference herein. A patient cable 350 has shared LED drive/ ID lines 352 that provide communications between the host instrument LED drivers 312 and ID reader 314 and the sensor LEDs 210 and ID element 230 via shared LED pinouts 240 (FIG. 2). Photodiode lines 354 provide communications between the sensor detector 220 and the host instrument signal conditioner 315.

SUMMARY OF THE INVENTION

FIG. 4 illustrates a sensor 400 having an alternative configuration of LEDs 410, photodiode 420 and sensor ID 430 from that described with respect to FIG. 2, above. In particular, the LEDs 410 have separate LED pinouts 402, the ID element 430 has separate ID element pinouts 405, and the photodiode 420 has separate photodiode pinouts 406.

FIG. 5 illustrates a pulse oximetry system 500 configured for the alternative configuration sensor 400. The pulse oximetry system 500 has a host instrument 510 and patient cable 550, as described with respect to FIGS. 2-3 above, except that the LED drive lines 532 and ID lines 534 are separate rather than shared and provide communications to LEDs 410 (FIG. 4) and an ID element 430 (FIG. 4) via separate LED pinouts 402 (FIG. 4) and ID element pinouts 405 (FIG. 4).

A host instrument 510 that is configured to read an ID element 430 over ID lines 534 that are separate from the LED drive lines 532, as described with respect to FIGS. 4-5, is incompatible with a sensor 200 (FIG. 3) having an ID element 230 (FIG. 3) wired in parallel with the LEDs 210 (FIG. 3), i.e. a sensor 200 (FIG. 3) having shared LED pinouts 240 (FIG. 2), as described with respect to FIGS. 2-3. A conversion cable that provides a mechanism for connecting a shared LED pinout sensor to a host instrument configured for a separate ID element pinout sensor is described in U.S. Pat. No. 6,349,228 entitled "Pulse Oximetry Sensor Adapter," which is assigned to Masimo Corporation, Irvine, Calif. and incorporated by reference herein. A conversion cable, however, does not prevent both a shared LED pinout sensor and a separate ID pinout sensor from being used with the same host instrument. For example, it is desirable to provide a mechanism whereby a host instrument configured for a separate ID pinout sensor may be reprogrammed so that the host instrument functions only with a shared LED pinout sensor.

One aspect of an encryption interface cable, which is configured to connect a host instrument to a physiological sensor is an ID signal input from the sensor and a LED drive signal input from a sensor port of the host instrument. The interface cable includes a data signal output to the sensor port, where the LED drive signal and the data signal provide a handshake to and from the host instrument. The handshake is responsive to the ID signal so as to enable a normal operation state of the host instrument.

An aspect of an encryption interface method of interconnecting a host instrument and a sensor comprises the steps of detecting if a sensor is valid, performing an encryption handshake with the host instrument upon valid sensor detection, and enabling normal physiological measurements with the host instrument only after completion of said encryption handshake. The detecting step may comprise the substeps of reading an ID element of the sensor, outputting an ID measurement corresponding to the ID element, and comparing the ID measurement to a plurality of predetermined values for known sensor types. The performing step may comprise the substeps of indicating sensor status to the host instrument, receiving a seed from the host instrument, generating a cipher text based upon the seed and transmitting the cipher text to the host instrument. The enabling step may comprise the substeps of receiving an indication of a successful handshake from the host instrument and closing a switch so as to connect LED drivers of the host instrument to LEDs of the sensor.

Another aspect of an encryption interface cable for connecting a host instrument to a sensor comprises a measurement means for reading a sensor ID element, a verification means for determining from the measurement means that the sensor is valid and for determining a corresponding sensor ID, a handshake means for establishing a communications link to the host instrument and for transmitting the sensor ID, and an adapter means for connecting the host instrument and the sensor upon establishing the link. The handshake means may comprise an encryption means for securing the communications link and a signal level means for transmitting data to and from a sensor port of the host instrument. The encryption means may comprise a key means for encrypting the data and a seed means for generating the key means. The encryption means may also comprise a password means for further encrypting said data.

DETAILED DESCRIPTION OF THE PREFERRED EMBODIMENT

System Overview

Figure 1:
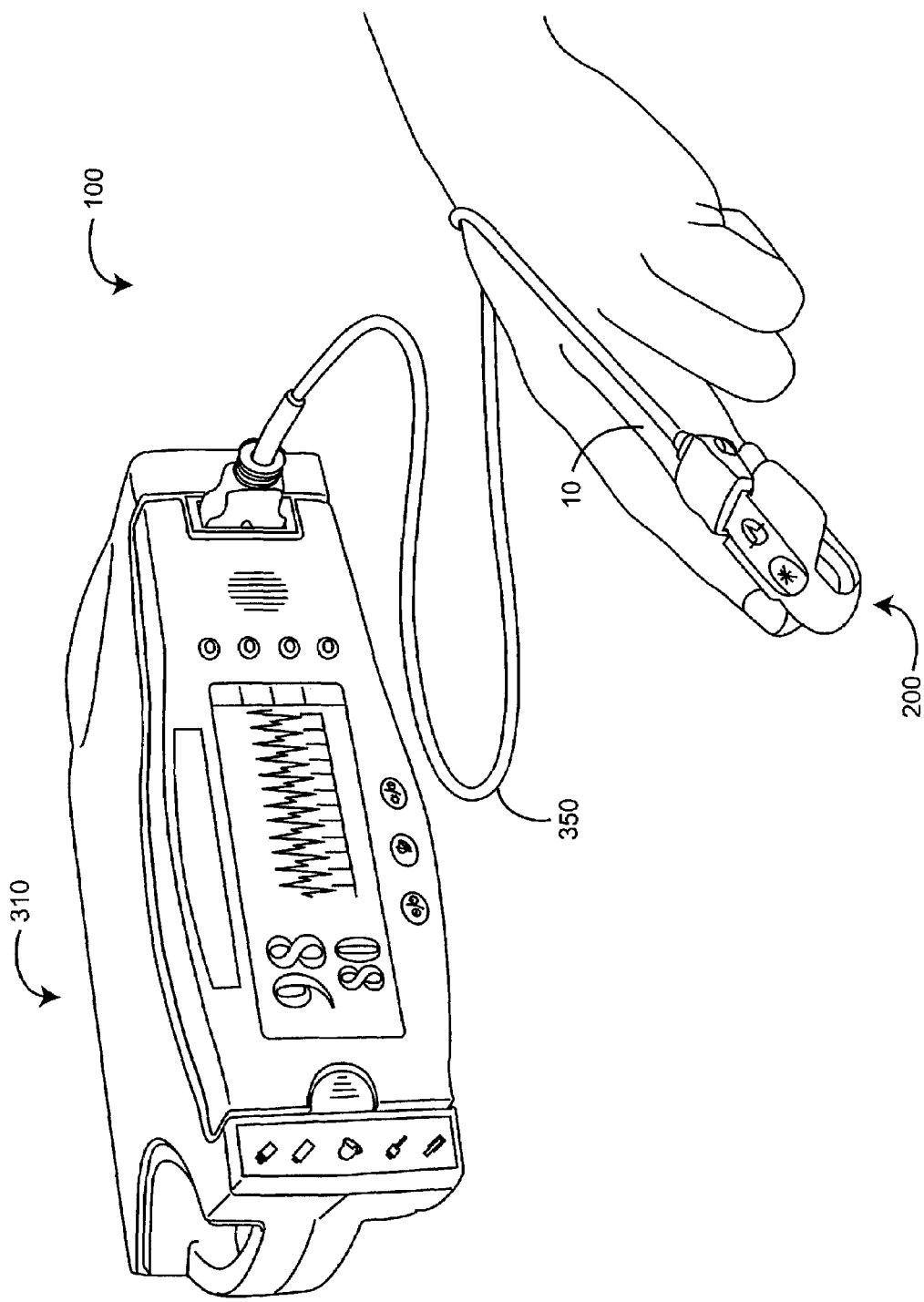
FIG. 1 is a perspective diagram illustrating a pulse oximetry system.
Figure 2:
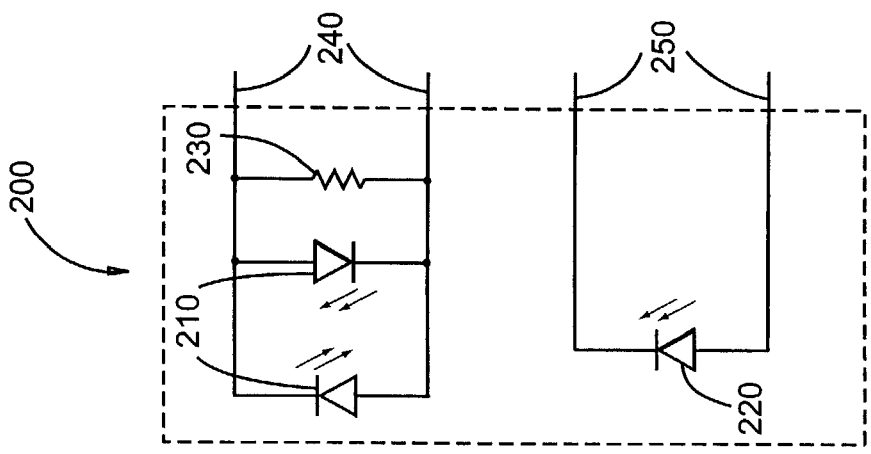
FIG. 2 is a schematic of a sensor having shared LED and ID element pinouts, i.e. a shared LED pinout sensor
Figure 5:
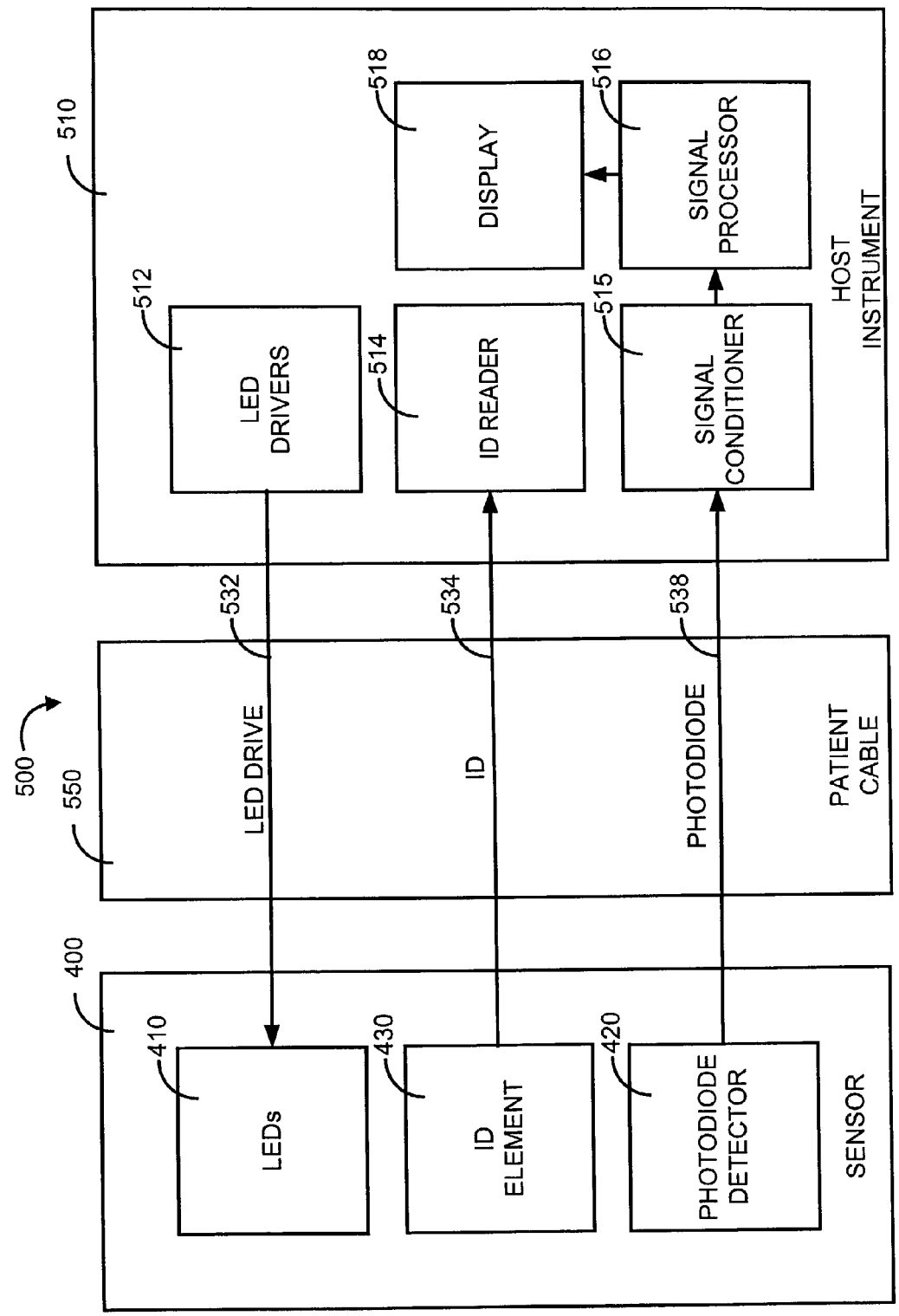
FIG. 5 is a functional block diagram of a pulse oximetry system configured for a separate ID pinout sensor.
Figure 6:
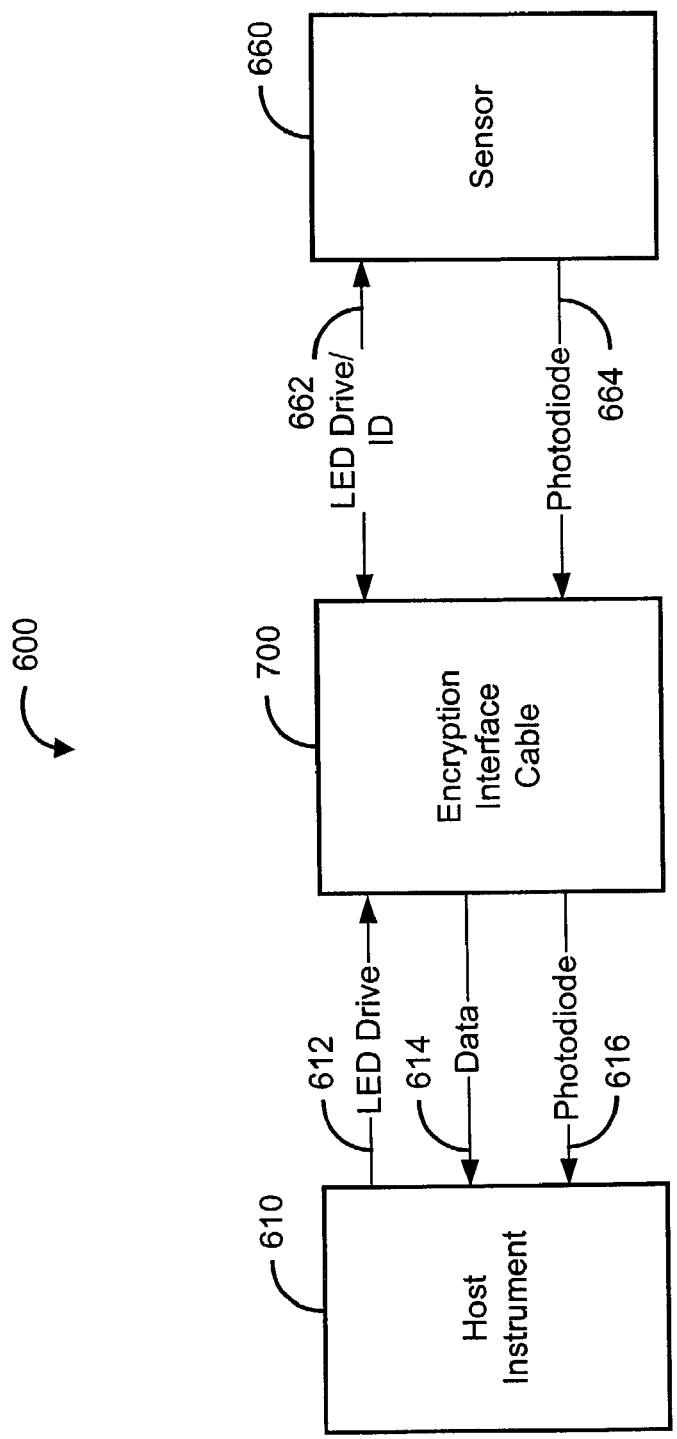
FIG. 6 is a block diagram of a pulse oximetry system utilizing an encryption interface cable.

FIG. 6 illustrates a pulse oximetry system 600 having a host instrument 610, an encryption interface cable 700 and a sensor 660. The sensor 660 may be a shared LED pinout sensor, as described with respect to FIG. 2 above, and the host instrument 610 may be compatible with a separate ID pinout sensor as described with respect to FIG. 5, above. That is, in one embodiment, the host instrument 610 is configured for separate LED drive lines 612 and separate ID ("data") lines 614, and the sensor is configured for shared LED drive/ID lines 662.

As shown in FIG. 6, an encryption interface cable 700, like a conversion cable, such as described in U.S. Pat. No. 6,349,228 referenced above, allows an otherwise incompatible shared LED pinout sensor 660 to be used with a host instrument 610 configured for a separate ID pinout sensor. However, unlike a conversion cable, one embodiment of an encryption interface cable 700 advantageously allows only authorized shared LED pinout sensors 660 to be used with the host instrument 610. Further, a host instrument configured for a separate ID pinout sensor can be advantageously programmed to function with an encryption interface cable 700 so as to be a host instrument 610 that is exclusively compatible with shared LED pinout sensors, without the necessity of hardware modifications to the host instrument.

Also shown in FIG. 6, the encryption interface cable 700 is a "smart" cable that checks for a valid host instrument 610 and a valid sensor 660. When the encryption interface cable ("cable") 700, valid sensor 660 and valid host instrument 610 are interconnected, the pulse oximetry system 600 will operate normally. Otherwise, the cable 700 will electrically disconnect the sensor LED drive/ ID lines 662 from the host instrument LED drive lines 612. The cable 700 determines host instrument validity by software "handshaking" using LED drive signals 702 (FIG. 7) on the LED drive lines 612 from the host instrument 610 to the cable 700 and data signals 704 (FIG. 7) on the data lines 614 from the cable 700 to the host instrument 610. The cable 700 determines the validity of the sensor 660 by reading a sensor ID signal 708 (FIG. 7) on the LED drive/ ID lines 708. The encryption interface cable 700 also determines if a sensor 660 is no longer connected and alerts the host instrument 610 accordingly. An encryption interface cable 700 is functionally described with respect to FIG. 7, below. The communications protocol between an encryption interface cable 700 and a host instrument 610 is described with respect to FIGS. 8-12, below. The cable 700 and host instrument 610 state transitions are described with respect to FIGS. 13-14, below.

Figure 7:
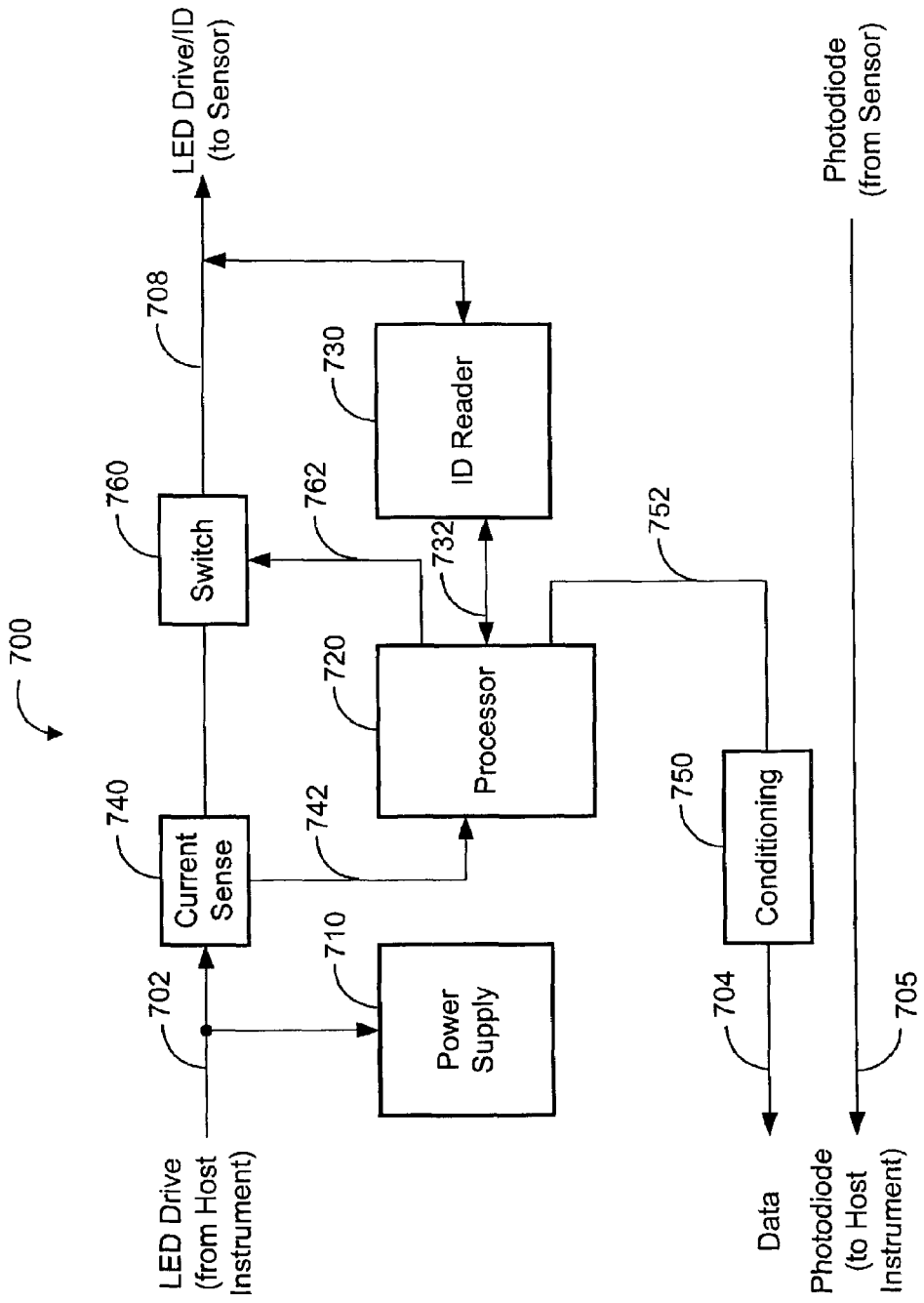
FIG. 7 is a block diagram of an encryption interface cable.

FIG. 7 illustrates an encryption interface cable ("cable") 700 having power supply 710, processor 720, ID reader 730, current sense 740, conditioning 750 and switch 760 circuits. The power supply 710 receives its current from one of the LED drive signals 702. In one embodiment, for example, during initial handshaking, the power supply 710 can draw about 50 mA from the host instrument 610 (FIG. 6). During normal operation, however, the maximum current drawn by the cable 700 is limited to about 3 mA, the rest used by the sensor LEDs. Further, this input current is available only during the LED-on time, which has a 25% duty cycle, for example.

Figure 3:
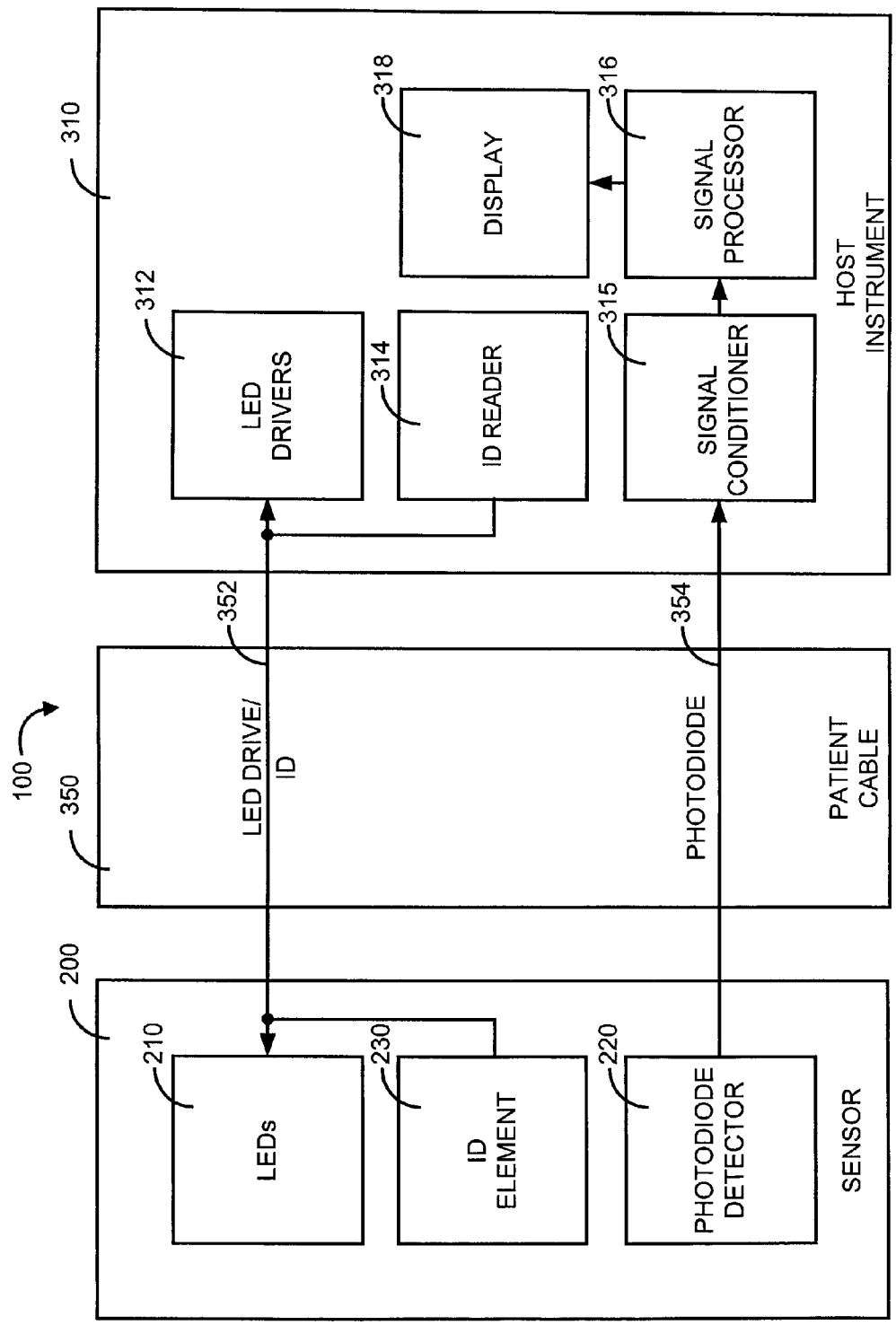
FIG. 3 is a functional block diagram of a pulse oximetry system configured for a shared LED pinout sensor.
Figure 4:
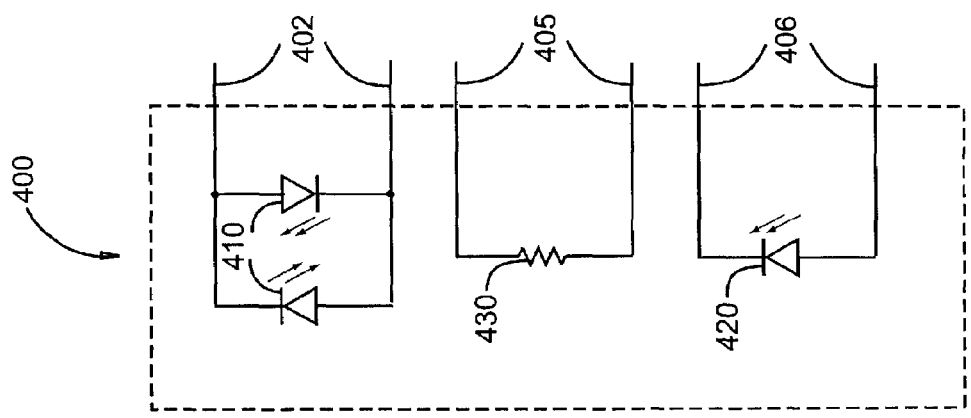
FIG. 4 is a schematic of a sensor having separate LED and ID element pinouts, i.e. a separate ID pinout sensor.

As shown in FIG. 7, the processor 720 is the master control for the cable 700, interfacing with the other cable circuits 730-760 to determine the validity of the host instrument 610 (FIG. 6) and the sensor 660 (FIG. 6). The ID reader circuit 730 inputs the ID signal 230 (FIG. 3) and outputs an ID measurement 732 to the processor 720. For example, in response to a processor command, the ID reader 730 may impose a voltage across a resistive ID element 230 (FIG. 2) and measure the resulting current, returning the measured value to the processor 720. In one embodiment, the ID reader 730 is used to determine the sensor type.

The current sense circuit 740 inputs the LED drive signal 702 and outputs a current measurement 742 to the processor 720. During the initial handshaking, the current sense circuit 740 is used to measure the data transmitted from the host instrument 610 (FIG. 6), such as described with respect to FIGS. 8 and 11, below. During normal operation, the current sense circuit 740 is used to determine whether a sensor 660 (FIG. 6) has been removed or a sensor failure has occurred.

The conditioning circuit 750 inputs transmit data 752 from the processor 720 and outputs a data signal 704 to the host instrument 610 (FIG. 6). Analog voltages of the data signal 704 represent "digital" values that the host instrument can measure, such as described with respect to FIG. 12, below.

The switch circuit 760 inputs a switch command 762 from the processor 720 and, in response, electrically connects or disconnects a sensor 660 (FIG. 6) to a host instrument 610 (FIG. 6). The processor 720 sets the switch 760 to an "open" position until the processor 720 determines that the cable 700 is connected to a valid host instrument 610 (FIG. 6) and an authorized sensor 660 (FIG. 6). During normal operation, the processor 720 sets the switch 760 to a "closed" position. The photodiode signal 705 is not switched and always remains connected.

Physically, the encryption interface cable 700 has a plastic housing and two cable portions. The plastic housing encloses a printed circuit board (PCB) and provides strain relief for the cable portions. One end of each cable portion terminates directly onto the PCB. Another end of a first cable portion is terminated with a patient cable connector that attaches to the sensor port of the host instrument 610 (FIG. 6). Another end of a second cable portion is terminated with a sensor connector that attaches to pinouts of the sensor 660 (FIG. 6). A sensor connector is described in U.S. Pat. No. 6,152,754, entitled "Circuit Board Based Cable Connector," which is assigned to Masimo Corporation, Irvine, Calif. and incorporated by reference herein.

Communications Overview

As shown in FIG. 6, communication between the cable 700 and the host instrument 610 is accomplished through the use of analog voltage and current levels to represent digital values and/or states. In particular, the host instrument 610 transmits to the cable 700 by providing an LED drive signal 702 (FIG. 7) having predetermined current levels, and the cable 700 transmits to the host instrument 610 by providing a data signal 704 (FIG. 7) having predetermined voltage levels. The cable 700 acts as the master, initiating a "handshake" communication sequence with the host instrument 610 using the data signal 704 (FIG. 7). Upon power on and after the host instrument 610 is initialized, the host instrument 610 samples the level of the data signal 704 (FIG. 7) to determine the status of the sensor 660. Upon power on, the cable 700 transmits a data signal 704 (FIG. 7) having a "display parameter" level or a "no parameter" level depending on whether a valid sensor 660 is or is not detected, respectively. If a valid sensor 660 is detected, the communication sequence is initiated between the cable 700 and the host instrument 610. After completion of the communication sequence, the pulse oximetry system 600 begins normal operation by performing patient monitoring. During normal operation, the cable 700 continually monitors for a sensor disconnect. If a sensor disconnect occurs, the cable 700 changes the data signal 704 (FIG. 7) to the no parameter level to alert the host instrument 610.

Figure 8:
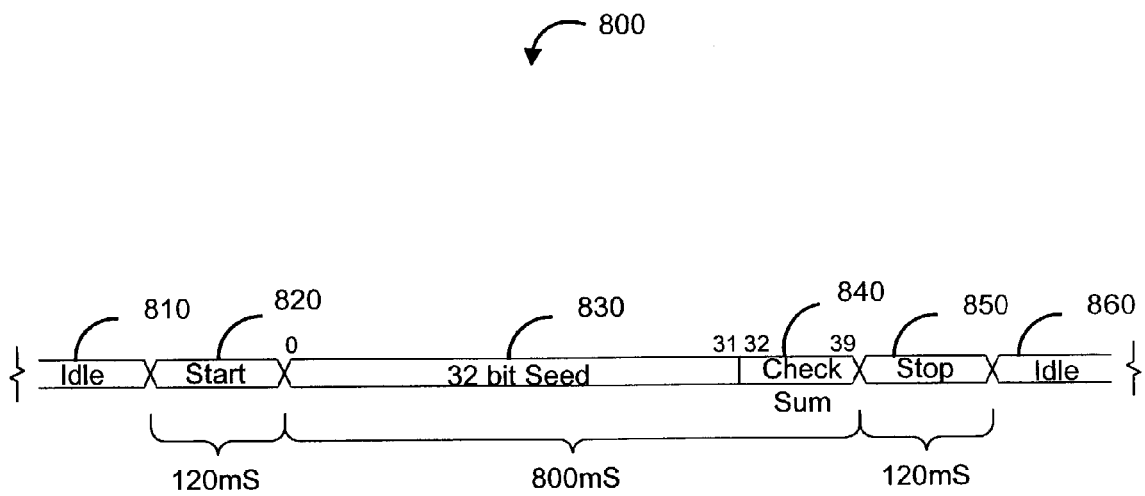
FIG. 8 is a timing diagram of a seed message.

In one embodiment, described with respect to FIGS. 8-11, below, the cable 700 and host instrument handshake consists of three messages: a seed message 800 (FIG. 8) transmitted by the host instrument 610; a sensor message 900 (FIG. 9) transmitted by the cable 700; and a host ready message 1100 (FIG. 11) transmitted by the host instrument 610. In another embodiment, described in further detail under the Alternative Protocols section below, the handshake includes a host ID message preceding the seed message 800 (FIG. 8).

Message Protocol

FIGS. 8-11 illustrate the message protocol for the seed, sensor and host ready messages, respectively. As listed in Tables 1 and 3, below, a start/stop level frames each of the messages. An idle level is presented whenever data is not being transmitted. Message data is represented by additional levels and transmitted least significant bit (LSB) first, as shown in FIG. 12, below, where each data level represents at least one bit. As listed in Tables 2 and 4, below, the level duration, i.e. the bit cell width, differs between a host instrument originated message, i.e. a seed message, and a cable originated message, i.e. a sensor message.

In one embodiment, described with respect to Tables 1 and 3 and FIGS. 8, 9 and 12, below, four levels each represent two bits. In an alternative embodiment, described in further detail under the Alternative Protocols section below, two levels each represent one bit.

Seed Message

FIG. 8 illustrates a seed message transmitted from the host instrument 610 (FIG. 6) to the cable 700 (FIG. 6) as an LED drive signal 702 (FIG. 7) having idle 810, 860; start and stop 820, 850; seed 830; and check sum 840 intervals. In one embodiment, the predetermined LED drive levels and the level durations are summarized in Tables 1-2, respectively.

TABLE 1

| LED Drive Signal Current Levels (Two Bits Per Cell) | |
|---|---|
| Logic Levels | LED Drive Level |
| Idle | 0 |
| Start/Stop | 255 |
| 00 | 102 |
| 01 | 135 |
| 10 | 168 |
| 11 | 204 |

TABLE 2

| Seed Message Level Durations | |
|---|---|
| Level | Level Duration |
| Logic Level Time | 40 mS |
| Idle | 120 mS minimum |
| Start/Stop | 120 mS |

The seed message 800 is 40 bits containing a 32 bit seed 830 and an 8 bit check sum 840. The seed 830 is used by both the host instrument 610 (FIG. 6) and the cable 660 (FIG. 6) to seed a random number generator. The generated 32 bit random number is used by both the host instrument 610 (FIG. 6) and the cable 660 (FIG. 6) as a final encryption key. The host instrument 610 (FIG. 6) uses a unique value for the seed for every handshake communication sequence. This value is based on a dynamic number such as a real time clock value. The seed 830 is transmitted to the cable 660 (FIG. 6) as plain text with no encryption. Both the cable 660 (FIG. 6) and the host instrument 610 (FIG. 6) then use the seed to independently generate the same final encryption key. Both the cable 660 (FIG. 6) and the host instrument 610 (FIG. 6) maintain the key internally, and it is never "in the open." The check sum 840 is 8 bits calculated by performing an exclusive OR operation on each byte of the 4 byte seed 830 and then bit-wise inverting the result, i.e. (Byte1 XOR Byte2 XOR Byte3 XOR Byte4) XOR 0xFF.

Sensor Message

Figure 9:
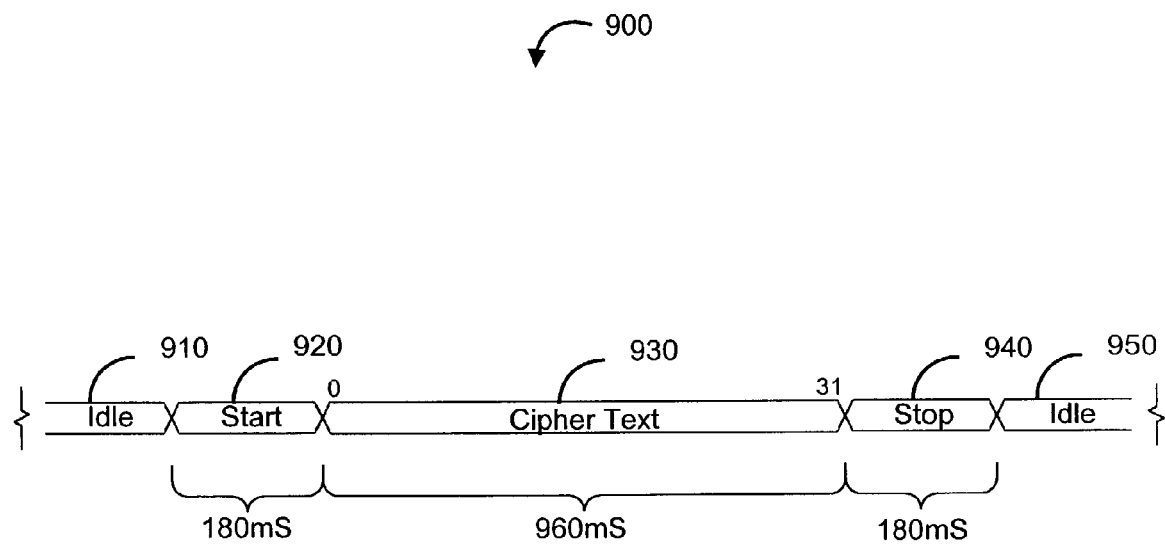
FIG. 9 is a timing diagram of a sensor message.

FIG. 9 illustrates a sensor message 900 transmitted from the cable 660 (FIG. 6) to the host instrument 610 (FIG. 6) as a data signal 704 (FIG. 7) having idle 910, 950; start and stop 920, 940; and cipher text 930 periods. The sensor message 900 contains 32 bits of encrypted cipher text 930, described with respect to FIG. 10, below. In one embodiment, the predetermined data signal levels and the level durations are summarized in Tables 3-4, respectively.

TABLE 3

Data Signal Voltage Levels (Two Bits Per Cell)

| Logic Levels | Analog Voltage Level (Typ) | Host Bin Voltage Level |
| --- | --- | --- |
| Start/Stop Level | 0.07 | 0.000-0.197 |
| Display Parameter, Sensor Connected (Idle) | 0.46 | 0.297-0.613 |
| 00 | 0.88 | 0.713-1.028 |
| 01 | 1.29 | 1.128-1.444 |
| 10 | 1.71 | 1.544-1.860 |
| 11 | 2.12 | 1.960-2.276 |
| No Parameter, No Sensor (Default) | 2.54 | 2.376-2.691 |
| Reserved | 2.95 | 2.791-3.092 |

TABLE 4

Timing Characteristics

| Level | Level Duration |
| --- | --- |
| Logic Level Time | 60 mS min. |
| Idle | 180 mS minimum |
| Start/Stop | 180 mS |
| Logic Level Transition Time | 300 uS max. |

Figure 10:
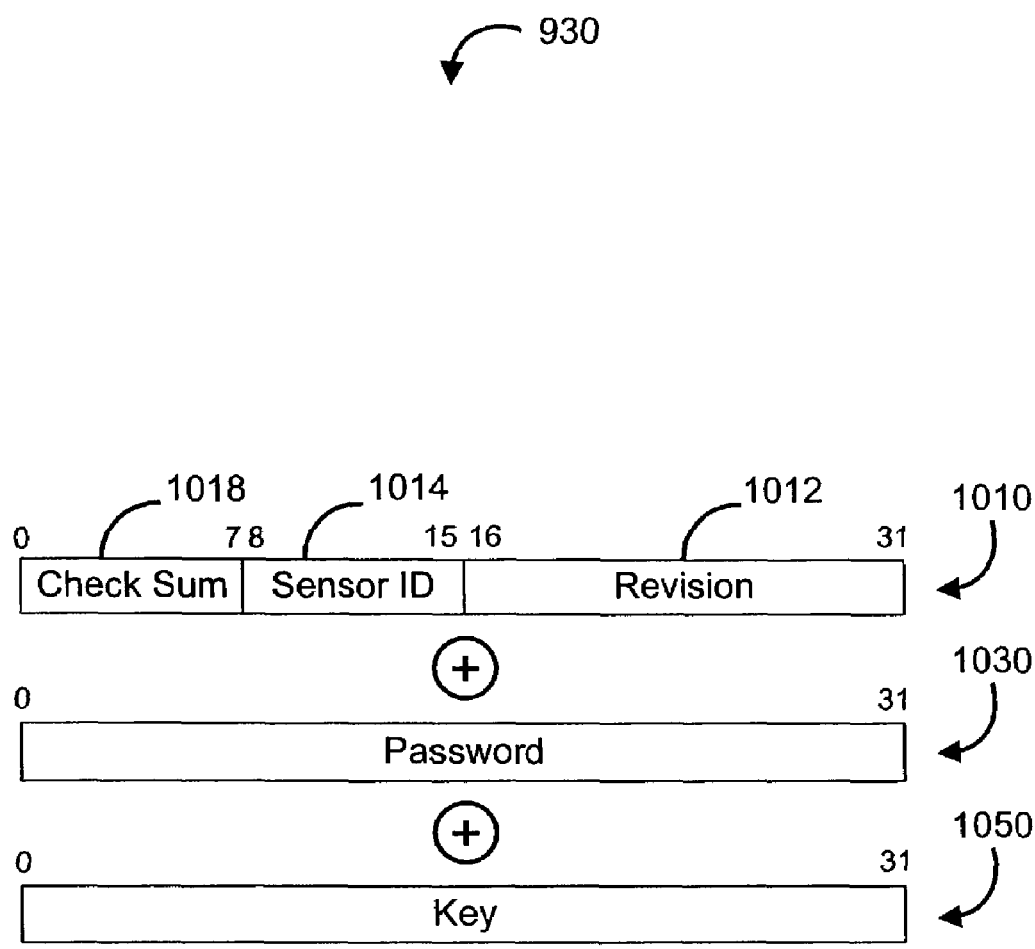
FIG. 10 is a component diagram of a sensor message cipher text.

FIG. 10 illustrates an encrypted cipher text 930 generated from a plain text message 1010, a password 1030 and a key 1050. The plain text message 1010 has a 16 bit revision field 1012, an 8 bit sensor ID field 1014 and a 8 bit checksum 1018. The revision field identifies the firmware version running on the cable processor 720 (FIG. 7). The sensor ID field 1014 identifies the sensor 660 (FIG. 6). Sensor ID values and corresponding identified sensor types for one sensor embodiment 200 (FIG. 2) are given in Table 5.

TABLE 5

Sensor ID

| Sensor ID: Value | Sensor ID |
| --- | --- |
| 0x00 | Unknown Sensor |
| 0x01 | NR |
| 0x02 | ADT |
| 0x03 | NEO |
| 0x04 | PDT |
| 0x05 | DCI |

The check sum 1018 is calculated by performing an exclusive OR (XOR) operation on each byte of the 3 byte revision 1012 and sensor ID 1014 fields. The result is then bit-wise inverted, i.e. (Byte1 XOR Byte2 XOR Byte3) XOR 0xFF. The password 1030 is a 32 bit constant known by both the host instrument 610 (FIG. 6) and the cable 660 (FIG. 6). The key 1050 is a 32 bit number generated as described with respect to FIG. 8, above.

As shown in FIG. 10, the cable 700 (FIG. 6) uses the key 1050 with two, bit-wise exclusive OR (XOR) operations to encrypt the plain text message 1010 and password 1030 into the encrypted cipher text 930. The first operation is an XOR of the plain text 1010 and the password 1030. The second operation is an XOR of the first operation's result and the generated key 1050. Conversely, the encrypted cipher text 930 is decrypted by the host instrument 610 (FIG. 6) with the same two XOR operations.

Host Ready Message

Figure 11:
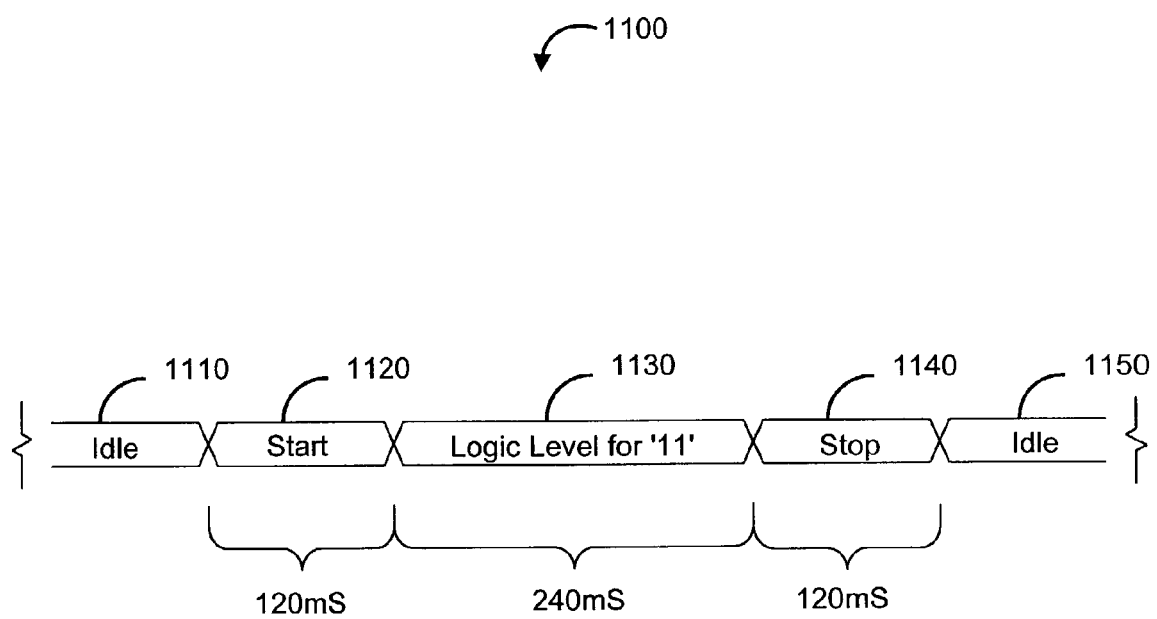
FIG. 11 is a timing diagram of a host ready message protocol.
Figure 12:
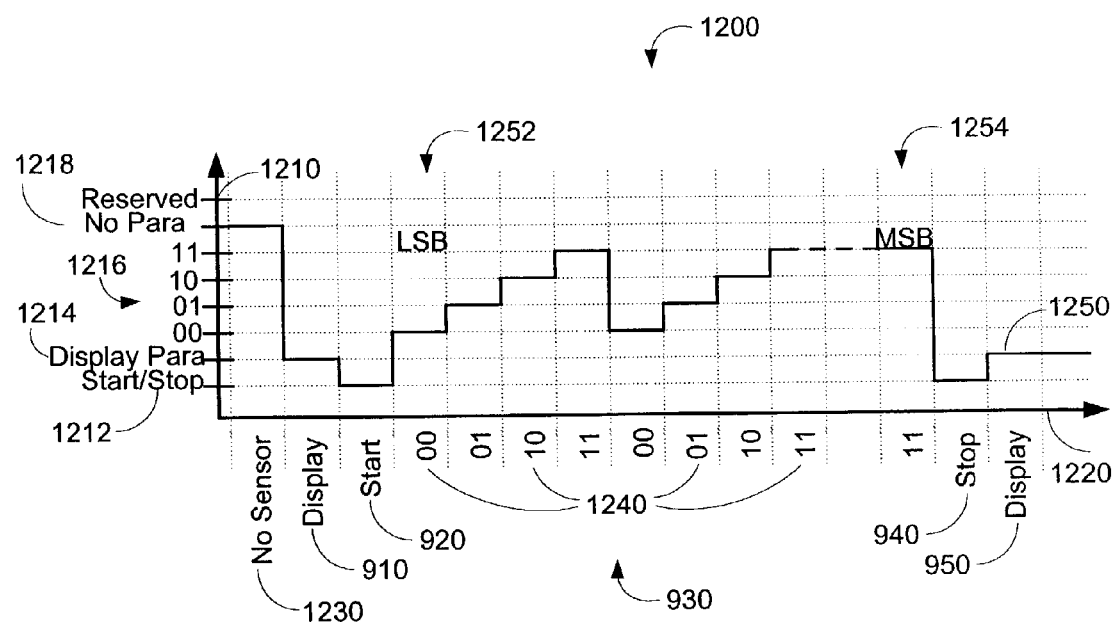
FIG. 12 is a voltage level vs. time graph of a sensor message waveform.

FIG. 11 illustrates a host ready message 1100 transmitted from the host instrument 610 (FIG. 6) to the cable 660 (FIG. 6) as an LED drive signal 702 (FIG. 7). The host ready message 1100 alerts the cable 660 (FIG. 6) that the host instrument 610 (FIG. 6) has received the sensor message 900 (FIG. 9), decoded it, and is now ready to drive the LEDs. The content of the host ready message 1100 is simply the host instrument's logic level 11 (e.g. LED drive level 204 in Table 1). The host instrument 610 (FIG. 6) presents the properly framed level for a minimum of 240 mS (6 bit pair cells) immediately following validated decoding of the cable's sensor message 900 (FIG. 9). The cable 660 (FIG. 6) waits to receive the host ready message 1100 immediately following its transmission of the sensor message 900 (FIG. 9).

FIG. 12 illustrates a graph 1200 having a voltage axis 1210 and a time axis 1220. The voltage axis 1210 has voltage levels 1212-1218 corresponding to the data signal 702 (FIG. 7), such as those listed in Table 3. Plotted on the graph 1200 is a sensor message waveform 1250 corresponding to a sensor message protocol 900 (FIG. 9), described above. The waveform 1250 has an initial period 1230 corresponding to a default "no parameter" level 1218. During idle periods 910, 950, the sensor message waveform 1250 has a "display parameter" level 1214. During start 920 and stop 950 periods, the waveform 1250 has a start/stop level 1212. During the cipher text period 930, the waveform 1250 has a least significant bits (LSB) portion 1252 followed by a most significant bits (MSB) portion 1254. During each cipher text portion 1252, 1254 the waveform 1250 may have multiple logic levels 1216 each corresponding to a logic level period 1240, such as listed in Tables 3-4.

Alternative Protocols

The communications protocol for the encryption interface cable is described above with respect to a three message handshake In an alternative embodiment, the handshake consists of four messages. A host ID message and a seed message are transmitted by the host instrument. Also, a sensor message is transmitted by the cable, and a host ready message is transmitted by the host instrument. The seed message, sensor message and host ready message are as described with respect to FIGS. 8, 9 and 11, above. The host ID message, like the other messages, is framed by start and stop levels. In a particular embodiment, the start and stop levels are of 120 ms duration. Between the start and stop levels, the host ID message has a LED drive level that identifies which host instrument is connected to the encryption interface cable. The cable uses this information, for example, to determine the LED modulation frequency. In a particular embodiment, the LED drive levels of 102 and 168, as described with respect to Table 1, above, identify one of two possible host instrument types, and the instrument type level has a 240 ms duration.

The communications protocol for the encryption interface cable is described above with respect to two bits per bit cell during both the seed message 800 (FIG. 8), as shown in Table 1, above, and the sensor message 900 (FIG. 9), as shown in Table 3, above, and FIG. 12. In an alternative embodiment, both the seed message and the sensor message are conveyed with one bit per cell. In this one bit embodiment, half as many logic levels are utilized and the message duration, excluding the start and stop levels, is twice as long, compared with the two bits embodiment. In a particular embodiment, the LED drive levels and the data signal voltage levels are described with respect to Tables 6 and 7, below. The timing characteristics are as described with respect to Tables 2 and 4, above. Thus, the combined 32-bit seed and check sum interval has a 1600 ms duration, as compared with the 800 ms duration of the two bit embodiment depicted in FIG. 8. Also, the cipher text interval has a 1920 ms duration, as compared with the 960 ms duration of the two bit embodiment depicted in FIG. 9.

TABLE 6

LED Drive Signal Current Levels (One Bit Per Cell)

| Logic Levels | LED Drive Level |
|---|---|
| Idle | 0 |
| Start/Stop | 255 |
| 0 | 102 |
| 1 | 135 |

TABLE 7

Data Signal Voltage Levels (One Bit Per Cell)

| Logic Levels | Analog Voltage Level (Typ) | Host Bin Voltage Level |
|---|---|---|
| Start/Stop Level | 0.07 | 0.000-0.197 |
| Display Parameter, Sensor Connected (Idle) | 0.46 | 0.297-0.613 |
| 0 | 0.88 | 0.713-1.028 |
| 1 | 1.29 | 1.128-1.444 |
| Reserved | 1.71 | 1.544-1.860 |
| Reserved | 2.12 | 1.960-2.276 |
| No Parameter, No Sensor (Default) | 2.54 | 2.376-2.691 |
| Reserved | 2.95 | 2.791-3.092 |

State Transitions

Figure 13:
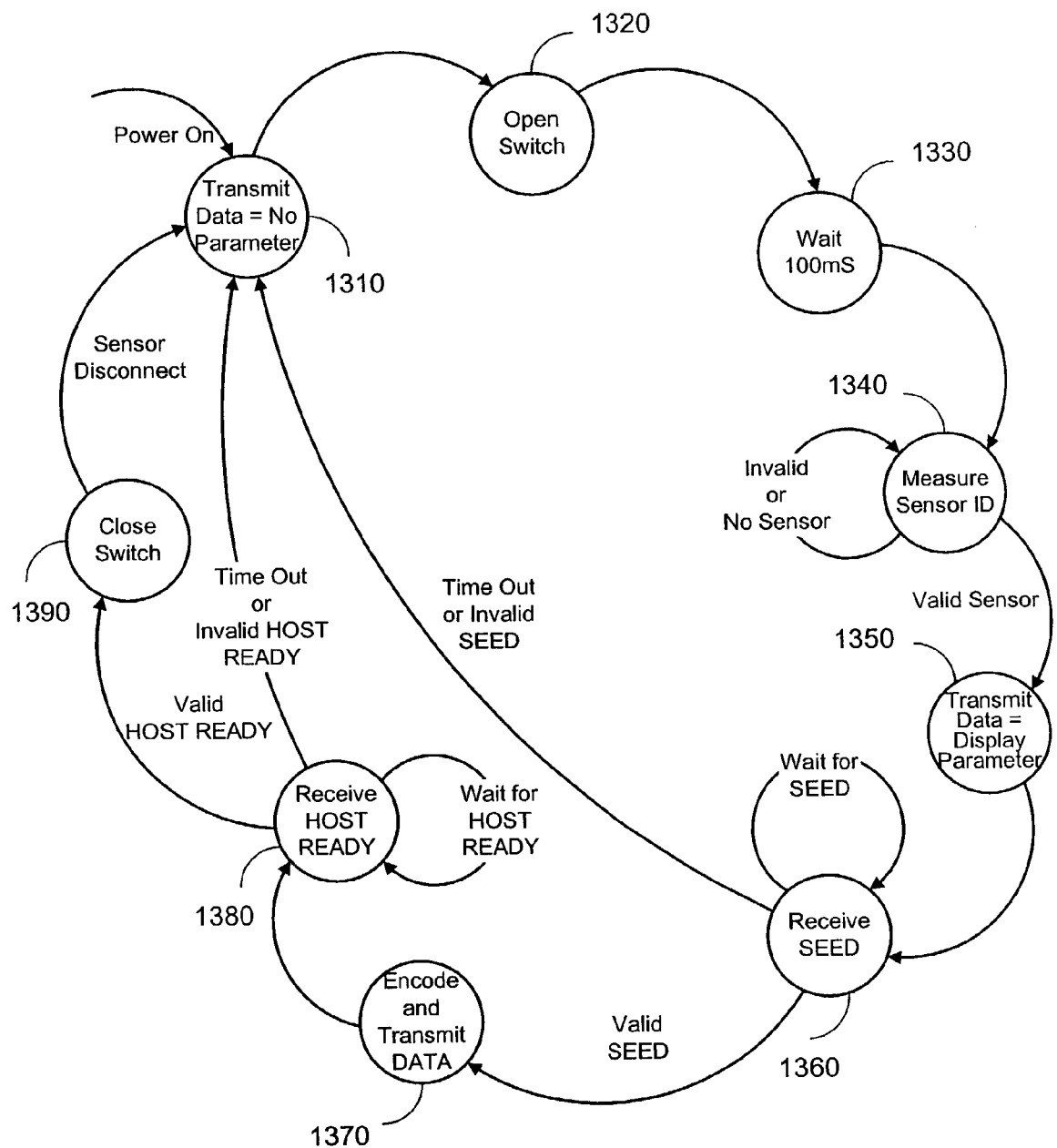
FIG. 13 is an encryption interface cable state transition diagram.
Figure 14:
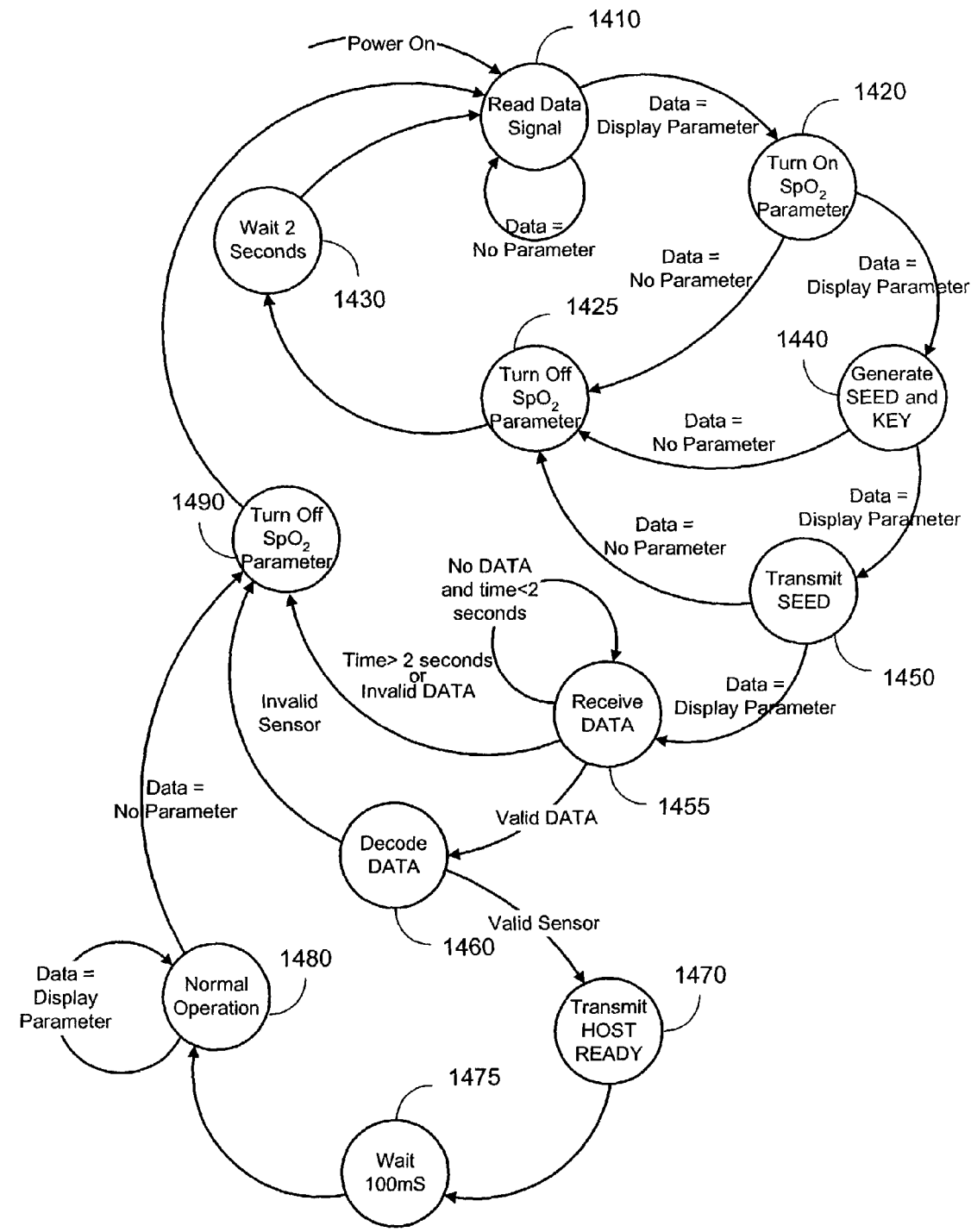
FIG. 14 is a host instrument state transition diagram.

FIGS. 13 and 14 illustrate cable 660 (FIG. 6) and host instrument 610 (FIG. 6) state transitions, respectively. The cable 660 (FIG. 6), functioning as the master, transmits to the host instrument 610 (FIG. 6) via the data signal 704 (FIG. 7). The host instrument 610 (FIG. 6) transmits to the cable 660 (FIG. 6) via the LED drive signal 702 (FIG. 7), as described above.

As shown in FIG. 13, upon "power on" the cable transmits a "no parameter" level data signal 1310; opens the switch 1320 so as to isolate the host LED drive lines 612 (FIG. 6) and corresponding LED drivers from the sensor LED lines 662 (FIG. 6) and corresponding LEDs. After a waiting period 1330, the cable measures the ID element 1340, as described with respect to FIG. 7, above. Upon detecting a valid sensor, the cable initiates handshaking by transmitting a "display parameter" level 1350.

Also shown in FIG. 13, the cable waits to receive the SEED from the host instrument 1360. Both the host instrument and the cable generate a KEY using the SEED, which are described with respect to FIG. 8, above. The cable generates DATA by double encoding sensor type information using the KEY and a password, as described with respect to FIG. 10, above, and transmits DATA to the host instrument 1370. The cable then waits to receive a HOST READY message 1380, as described with respect to FIG. 11, above. Upon receiving HOST READY, the cable closes the switch 1390, connecting the host instrument LED drivers to the sensor LEDs via the cable. At this time, the handshaking is complete, and the pulse oximetry system enters normal operation. During normal operation, the cable continually monitors for sensor disconnect. When a sensor is disconnected, the cable changes the data signal to a "no parameter" level 1310 to alert the host instrument. If the cable and the host instrument get out of synchronization, the cable will return the host instrument to its initial state by setting the data signal to a "no parameter" level 1310.

As shown in FIG. 14, after the host instrument is initialized, e.g. upon a power on, the host instrument samples the data signal 1410 so as to determine whether the cable has detected a valid sensor. When the host instrument detects a "display parameter" level, the host instrument displays a SpO$_2$ parameter window 1420. Then, the host instrument generates a SEED 1440, generates its own KEY, and transmits the SEED to the cable 1450, as described with respect to FIG. 8, above. The host instrument waits to receive DATA from the cable in response 1455, as described with respect to FIG. 13, above. If the host instrument receives valid DATA, the host instrument decodes DATA 1460 and transmits a HOST READY message to the cable 1470 in response. At this time, the handshaking is complete, and, after waiting a predetermined time period 1475, the host instrument begins normal operation 1480. If the host instrument detects a "no parameter" level during handshaking 1420-1450 or during normal operation 1480, then the SpO$_2$ parameter window is turned off 1425, 1490, and the host instrument is returned to its initial state 1410. Similarly, if during the receive DATA state 1455, the host instrument fails to receive valid DATA, the SpO$_2$ parameter window is turned off 1490, and the host instrument is returned to its initial state 1410.

The encryption interface cable is disclosed above in connection with a host instrument configured for a separate ID pinout sensor, interfaced to a shared LED pinout sensor. Alternative encryption interface cable embodiments, however, may have a host instrument configured for any sensor pinout, interfaced to any sensor. For example, an encryption interface cable may be adapted for a host instrument configured for a shared LED pinout sensor, interfaced to a separate ID pinout sensor.

Further, an encryption interface cable may be adapted for a host instrument configured to read one type of ID element, interfaced to a sensor having another type of ID element. For example, an encryption interface cable may be adapted for a host instrument originally configured to read a memory ID element, interfaced to a sensor having a resistive ID element.

Advantageously, a host instrument may be programmed to function normally only via an interface cable that successfully completes an encrypted handshake. Also, the encryption interface cable may be configured to accept only sensors that have a particular configuration and that provide a particular ID signal. In this manner, a host instrument may be programmed without hardware modification to function normally only with authorized sensors, and those sensors may be different in configuration and/or have a different ID element than sensors originally designed for the host instrument.

An encrypted handshake is disclosed above in connection with a public seed used to generate a private key for both the host instrument and the encryption interface cable. Further, the key is disclosed above in connection with creating a particular cipher text using XOR operations. One of ordinary skill in the art will recognize that an encryption handshake may use various key generation or key distribution schemes and various encryption and decryption algorithms, such as DES for example, to generate various encrypted messages.

An encryption interface cable has been disclosed in detail in connection with various embodiments. These embodiments are disclosed by way of examples only. One of ordinary skill in the art will appreciate many variations and modifications of an encryption interface cable within the scope of the claims that follow.

What is claimed is:

1. An interface method of interconnecting a patient monitoring instrument and a noninvasive sensor usable with said patient monitor to supply said patient monitor signals processable to determine one or more physiological parameters of a monitored patient, the interface method comprising the steps of:
   detecting if said sensor is valid by determining sensor identification information using at least a light emitter drive signal line disposed within a cable and an identification reader disposed within said cable;
   performing an encryption handshake with said patient monitoring instrument upon valid sensor detection, said performing the encryption handshake comprising dynamically generating a private encryption key based at least partly on a public seed;
   enabling normal physiological measurements processing with said patient monitoring instrument after successful completion of said encryption handshake; and
   providing light emitter drive signals to the sensor using the light emitter drive signal line.

2. The interface method of claim 1 wherein said detecting step comprises the substeps of:
   reading an identification element of said sensor
   outputting an identification measurement corresponding to said identification element; and
   comparing said identification measurement to a plurality of predetermined values for known sensor types.

3. The interface method of claim 1 wherein said performing step further comprises the substeps of:
   indicating sensor status to said patient monitoring instrument;
   receiving a said public seed from said host patient monitoring instrument;
   generating a cipher text based upon said private key; and
   transmitting said cipher text to said patient monitoring instrument.

4. The interface method of claim 3 wherein said indicating substep comprises the substeps of:
   outputting a data signal to a sensor port of said patient monitoring instrument; and
   varying voltage levels of said data signal corresponding to said sensor status.

5. The interface method of claim 3 wherein said receiving substep comprises the substeps of:
   inputting a light emitter drive signal from said patient monitoring instrument over said light emitter drive signal line; and
   varying current levels on said light emitter drive signal line corresponding to at least one data bit.

6. The interface method of claim 3 wherein said generating substep further comprises the substeps of:
   deriving a sensor identification corresponding to a type of said sensor based upon said identification measurement; and
   combining said sensor identification and said key.

7. The interface method of claim 6 wherein said combining substep comprises the substeps of:
   storing a predetermined password;
   incorporating said sensor identification into a data word; and
   performing an "exclusive or" of said data word, said password and said key.

8. The interface method of claim 3 wherein said transmitting substep comprises the substeps of:
   outputting a data signal to a sensor port of said patient monitoring instrument; and
   varying voltage levels on said data signal corresponding to at least one data bit.

9. The interface method of claim 1 wherein said enabling step comprises the substeps of:
   receiving an indication of a successful handshake from said patient monitoring instrument; and
   closing a switch so as to connect said light emitter drive signal line of said patient monitoring instrument to light emitters of said sensor.

10. A cable enabling communication between a host patient monitoring instrument to and a noninvasive optical sensor, the cable comprising:
    a measurement means for reading a sensor identification element using a sensor drive line, wherein the drive line is also used to drive a one or more light emitters;
    a verification means for determining from said measurement means that said sensor is valid and for determining a corresponding sensor identification;
    a handshake means for establishing said communication and for transmitting said sensor identification, said handshake means including at least a portion of an LED signal conductor, said handshake means comprising encryption means for dynamically generating an encryption key based at least partlv on a seed in response to receiving a handshaking message; and
    an adapter means for connecting said host patient monitoring instrument and said sensor upon establishing said communication.

11. The cable according to claim 10 wherein said handshake means comprises:
    a signal level means for transmitting data to and from a sensor port of said patient monitoring instrument.

12. The cable according to claim 10 wherein said encryption means comprises:
    a key for encrypting said data.

13. The cable according to claim 10 wherein said encryption means further comprises a password means for further encrypting said data.

14. A cable for providing communication between electronics of a host patient monitoring instrument and a noninvasive physiological sensor configured to be positioned proximate body tissue and configured to provide said patient monitoring instrument with signals indicative of one or more physiological parameters of a monitored patient, said cable comprising:
    an LED drive signal line disposed within said cable, the LED drive signal line used to send LED drive signals to LEDs of a said noninvasive physiological sensor;
    a data signal line disposed within said cable;
    an identification reader disposed within said cable; and
    wherein prior to acquisition of measurement data, said LED drive signal line and said identification reader are also used to determine whether said a sensor is valid, and said LED drive signal line and said data signal line are used to conduct a handshake to and from said host patient monitoring instrument, said handshake responsive to said determination, wherein said handshake comprises a message operative to dynamically initiate an encryption key generation process based at least partly on a seed.

15. A cable configured to provide communication between a host patient monitoring instrument and a noninvasive physiological sensor configured to be positioned proximate body tissue and configured to provide said patient monitoring instrument with signals indicative of one or more physiological parameters of a monitored patient, said cable comprising:

a patient monitoring instrument port including:

a patient monitoring input configured to receive sensor light emitter drive signals from a said hest patient monitoring instrument, and a patient monitoring output configured to transmit at least validation data to said patient monitoring instrument;

a sensor port configured to provide communications with said noninvasive physiological sensor; and a processor configured to:

determine sensor identification information from said sensor light emitter drive signals and output said validation data, and generate an encryption key dynamically based at least partly on a seed in response to receiving a signal from the patient monitoring instrument.

16. The cable of claim 15, further comprising a second patient monitoring output configured to output a photodiode signal to said patient monitoring instrument.

17. The cable of claim 15, wherein said sensor port comprises a first sensor output, configured to output at least said sensor light emitter drive signal and a first sensor input, configured to receive at least a photodiode signal from a physiological sensor.

18. The cable of claim 17, further comprising an identification reader configured to determine at least a sensor identification from said sensor light emitter drive signal.

19. The cable of claim 18, wherein said identification reader communicates with said sensor through said sensor output in order to determine said sensor identification.

20. The cable of claim 18, wherein said processor comprises said identification reader.

21. The cable of claim 15, wherein said seed is generated by said patient monitoring instrument.

22. The cable of claim 21, further comprising a current sense circuit that is responsive to said sensor light emitter drive signal to output a current measurement to said processor and wherein said processor is responsive to said current measurement to determine said seed generated by said patient monitoring instrument.

23. The cable of claim 21, further comprising a conditioning circuit configured to condition the validation data for communication to said patient monitoring instrument.

24. The cable of claim 15, further comprising a switch having a closed state connecting said sensor light emitter drive signal to said sensor port and an open state disconnecting said sensor drive signal from said sensor, said switch including a control input to said switch determining said open state and said closed state, said processor generating said control in response to an operation state.

* * * * *